(12) United States Patent
Bunquin et al.

(10) Patent No.: US 11,738,331 B2
(45) Date of Patent: Aug. 29, 2023

(54) SUPPORTED MULTIMETALLIC CATALYSTS FOR OXIDATIVE DEHYDROGENATION OF ALKANES

(71) Applicant: UCHICAGO ARGONNE, LLC, Chicago, IL (US)

(72) Inventors: Jeffrey C. Bunquin, Westmont, IL (US); Magali S. Ferrandon, Downers Grove, IL (US)

(73) Assignee: UChicago Argonne, LLC, Chicago, IL (US)

( * ) Notice: Subject to any disclaimer, the term of this patent is extended or adjusted under 35 U.S.C. 154(b) by 342 days.

(21) Appl. No.: 17/060,693

(22) Filed: Oct. 1, 2020

(65) Prior Publication Data

US 2021/0053032 A1 Feb. 25, 2021

Related U.S. Application Data

(62) Division of application No. 15/688,699, filed on Aug. 28, 2017, now Pat. No. 10,828,621.

(51) Int. Cl.

| | |
|---|---|
| *B01J 23/34* | (2006.01) |
| *C07C 5/48* | (2006.01) |
| *B01J 23/889* | (2006.01) |
| *B01J 27/24* | (2006.01) |
| *B01J 37/02* | (2006.01) |
| *B01J 37/34* | (2006.01) |

(52) U.S. Cl.
CPC .......... *B01J 23/34* (2013.01); *B01J 23/8892* (2013.01); *B01J 27/24* (2013.01); *B01J 37/024* (2013.01); *B01J 37/347* (2013.01); *C07C 5/48* (2013.01); *C07C 2521/04* (2013.01); *C07C 2521/06* (2013.01); *C07C 2521/08* (2013.01); *C07C 2523/22* (2013.01); *C07C 2523/26* (2013.01); *C07C 2523/34* (2013.01); *C07C 2523/755* (2013.01); *C07C 2523/889* (2013.01); *C07C 2527/24* (2013.01)

(58) Field of Classification Search
None
See application file for complete search history.

(56) References Cited

U.S. PATENT DOCUMENTS

| | | | |
|---|---|---|---|
| 3,539,651 | A | 11/1970 | Hepp et al. |
| 4,005,985 | A | 2/1977 | Hutson, Jr. |
| 4,041,099 | A | 8/1977 | Hutson, Jr. |
| 4,176,140 | A | 11/1979 | Bertus et al. |

(Continued)

FOREIGN PATENT DOCUMENTS

| | | |
|---|---|---|
| CN | 102417432 A | 4/2012 |
| DE | 20 26 104 A1 | 12/1970 |

(Continued)

OTHER PUBLICATIONS

Agafonov, et al., "Kinetics and mechanism of the oxidative dehydrogenation of isobutane on cobalt, nickel, and manganese molybdates," Kinetics and Catalysis 48(2), pp. 255-264 (2007).

(Continued)

*Primary Examiner* — Colin W. Slifka
(74) *Attorney, Agent, or Firm* — Foley & Lardner LLP (57) ABSTRACT

A catalyst for oxidative dehydrogenation of alkanes includes a substrate including an oxide; at least one promoter including a transition metal or a main group element of the periodic table; and an oxidation-active transition metal. The catalyst is multimetallic.

5 Claims, 3 Drawing Sheets

(56) References Cited

U.S. PATENT DOCUMENTS

| | | | |
|---|---|---|---|
| 5,362,378 | A | 11/1994 | Borghard et al. |
| 6,191,064 | B1 | 2/2001 | Wu et al. |
| 6,414,209 | B1 | 7/2002 | Herskowitz et al. |
| 6,635,598 | B2 | 10/2003 | Dongara et al. |
| 6,756,340 | B2 | 6/2004 | Voskoboynikov et al. |
| 7,034,195 | B2 | 4/2006 | Schindler et al. |
| 7,550,637 | B2 | 6/2009 | Lowe et al. |
| 7,972,569 | B2 | 7/2011 | Elam et al. |
| 8,318,248 | B2 | 11/2012 | Elam et al. |
| 2006/0004228 | A1 | 1/2006 | Hazin |
| 2006/0235243 | A1 | 10/2006 | Fukumoto |
| 2013/0072738 | A1 | 3/2013 | Jung et al. |
| 2014/0309470 | A1 | 10/2014 | Park et al. |

FOREIGN PATENT DOCUMENTS

| | | |
|---|---|---|
| DE | 24 01 955 A1 | 7/1975 |
| EP | 0 986 22 A2 | 1/1984 |
| EP | 2 832 716 A1 | 2/2015 |
| GB | 0 904 699 A | 8/1962 |
| IT | 1409944 B1 | 9/2014 |
| KR | 2011078241 A | 7/2011 |
| KR | 2012007764 A | 1/2012 |
| KR | 1020140013387 A | 2/2014 |
| KR | 1020140085776 A | 7/2014 |
| KR | 1477413 B1 | 12/2014 |
| KR | 1020140143591 A | 12/2014 |
| KR | 2015037503 A | 4/2015 |
| KR | 101485697 B1 | 1/2016 |
| WO | WO-2010/057663 A1 | 5/2010 |
| WO | WO-2013/021020 A1 | 2/2013 |
| WO | WO-2013/021034 A1 | 2/2013 |
| WO | WO-2014/128717 A2 | 8/2014 |

OTHER PUBLICATIONS

Ai-Ju, et al., "Study on M—Fe—O Catalysts for Oxidative Dehydrogenation of Propane to Propene," Journal of Molecular Catalysts (China) 21(5), pp. 447-452 (2007).

Ai-Ju, et al., "The study on catalytic performance of fine ferrite derived from open-heath dust," Gongneng Cailiao 38(6), pp. 927-930 (2007).

Ajayi, et al., "n-Butane dehydrogenation over mono and bimetallic MCM-41 catalysts under oxygen free atmosphere," Catalysis Today 204, pp. 189-196 (2013).

Al-Zahrani, et al., "Activities of y-Al2O3-Supported Metal Oxide Catalysis in Propane Oxidative Dehydrogenation," Catalysis Letters 85(1-2), pp. 57-67 (2003).

Bachiller-Baeza, et al., "Improved performance of carbon nanofiber-supported palladium particles in the selective 1,3-butadiene hydrogenation: Influence of carbon nanostructure, support functionalization treatment and metal precursor," Catalysis Today 249, pp. 63-71 (2015).

Baldi, et al., "Propane catalytic oxidation and oxy-dehydrogenation over manganese-based metal oxides," Studies in Surface Science and Catalysis 119, pp. 635-640 (1998).

Baldia, et al., "Evaluation of the mechanism of the oxy-dehydrogenation of propane over manganese oxide," Applied Catalysis A: General 173(1), pp. 61-74 (1998).

Ballarini, et al., "Use of Al2O3—SnO2 as a support of Pt for selective dehydrogenation of light paraffins," Catalysis Today 133-135, pp. 28-34 (2008).

Berhault, et al., "Preparation or nanostructurea Pd particles using a seeding synthesis approach—Application to the selective hydrogenation of buta-1,3-diene," Applied Catalysis A: General 327(1), pp. 32-43 (2007).

Bocanegra, et al., "Behavior of PtPb/MgAl2O4 catalysts with different Pb contents and trimetallic PtPbIn catalysts in n-butane dehydrogenation," Applied Catalysis A: General 468, pp. 135-142 (2013).

Bocanegra, et al., "Characterization and catalytic behavior in the n-butane dehydrogenation of trimetallic InPtSn/MgAl2O4 catalysts," Applied Catalysis A: General, pp. 49-56 (2007).

Bocanegra, et al., "Effect of the Synthesis Method of MgAl2O4 and of Sn and Pb Addition to Platinum Catalysts on the Behavior in n-Butane Dehydrogenation," Industrial & Engineering Chemistry Research 49(9), pp. 4044-4054 (2010).

Bocanegra, et al., "n-Butane Dehydrogenation on PtSn Supported on MAl2O4 (M: Mg or Zn) Catalysts," Catalysis Letters 96(3-4), pp. 129-140 (2004).

Cadus, et al., "Characterization of Mo—MnO catalyst for propane oxidative dehydrogenation," Applied Catalysis A: General 233(1-2), pp. 239-253 (2002).

Cadus, et al., "Highly effective molybdena-manganese catalyst for propane oxidative dehydrogenation," Catalysis Letters 69(3-4), pp. 199-202 (2000).

Callejas, et al., "Catalytic dehydrogenation of n-butane in a fluidized bed reactor with separate coking and regeneration zones," Studies in Surface Science and Catalysis 130, pp. 2717-2722 (2000).

Chen, et al,. "Butane Dehydrogenation Reaction on Sulfur Poisoned Group 10 Metal/SiO2 Catalysts," Journal of the Chinese Chemical Society 43(5), pp. 379-386 (1996).

Deepyaman, et al., "Selective hydrogenation of 1,3-butadiene in mixture with isobutene on a Pd/a-alumina catalyst in a semi-batch reactor," Chemical Engineering Science 62(17), pp. 4544-4557 (2007).

El Kolli, et al., "Bimetallic Au-Pd catalysts for selective hydrogenation of butadiene: Influence of the preparation method on catalytic properties," Journal of Catalysis 297, pp. 79-92 (2013).

Ermini, et al., "Propane oxydehydrogenation over alumina-supported vanadia doped with manganese and potassium," Applied Catalysis A: General 198(1-2), pp. 67-79 (2000).

Gomez, et al., "A theoretical view of 1,3-butadiene selective hydrogenation toward cis-2-butene on Pd—Ni layered catalyst," Applied Surface Science 353, pp. 820-828 (2015).

Hou, et al., "Effect of oxide supports on Pd-Ni bimetallic catalysts for 1,3-butadiene hydrogenation," Applied Catalysis A: General 490, pp. 17-23 (2015).

Hou, et al., "Selective hydrogenation of 1,3-butadiene on Pd-Ni bimetallic catalyst: from model surfaces to supported catalysts," Journal of Catalysis 316, pp. 1-10 (2014).

Huang, et al., "Optimization of process conditions for butane dehydrogenation catalyst L-78," Shihua Jishu Yu Yingyong (Petrochemical Technology & Application) 32(2), pp. 131-134 (2014).

Inaba, et al., "Dehydrogenation and Isomerization of n-Butane or Isobutane Over Cr Catalysts Supported on Zeolites," Catalysis Letters 84(3-4), pp. 273-279 (2002).

Insorn, et al., "Selective hydrogenation of mixed C4 containing high vinyl acetylene by Mn—Pd, Ni—Pd and Ag—Pd on Al2O3 catalysts," Catalysis Today 256(2), pp. 223-230 (2015).

Jibril, "Effects of Food Compositions on Oxidative Dehydrogenation of Propane over Mn—P—O Catalyst," Industrial & Engineering Chemistry Research 44(4), pp. 702-706 (2005).

Jibril, et al., "Propane Oxidative Dehydrogenation over Metal Pyrophosphates Catalysts," Catalysis Letters 74(3-4), pp. 145-148 (2001).

Jugnet, et al., "Selective hydrogenation of 1,3-butadiene on Pt3Sn(111) alloys: comparison to Pt(111)," Journal of Catalysis 229(1), pp. 252-258 (2005).

Kikuchi, et al., "Dehydrogenation of n-Butane to Butadiene over Pt—Sn/MgO—Al2O3," Journal of the Japan Petroleum Institute 55(1), pp. 33-39 (2012).

Kikuchi, et al., "Effect of Sn Addition on n-Butane Dehydrogenation over Alumina-supported Pt Catalysts Prepared by Co-impregnation and Sol-gel Methods," Journal of the Japan Petroleum Institute 55(3), pp. 206-213 (2012).

Kondratenko, et al., "Characterization of vanadium-oxide-based catalysis for the oxidative dehydrogenation of propane to propene," Topics in Catalysis 15(2-4), pp. 175-180 (2001).

Larese, et al., "Alumina- and Zirconia-Alumina-Loaded Tin-Platinum. Surface Features and Performance for Butane Dehydrogenation," Langmuir 16(25), pp. 10294-10300 (2000).

(56) References Cited

OTHER PUBLICATIONS

Lee, et al., "Platinum-Tin Nano-Catalysts Supported on Alumina for Direct Dehydrogenation of n-Butane," Journal of Nanoscience and Nanotechnology 15(10), pp. 8305-8310 (2015).
Lee, et al., "Selective hydrogenation of 1,3-butadiene on TiO2-modified Pd/SiO2 catalysts," Applied Catalysis A: General 244(1), pp. 83-91 (2003).
Li, et al., "Selective Alkane Oxidation by Manganese Oxide: Site Isolation of MNOx Chains at the Surface of MnWO4 Nanorods", Angewandte Chemie 55(12), pp. 4092-4096 (2016).
Liu, et al., "Hydrogenation of 1,3-butadiene over Au and Pt/SiO2—N catalysts at low temperature," Catalysis Communications 67, pp. 72-77 (2015).
Liu, et al., "Single Gold Atoms in Heterogeneous Catalysis: Selective 1,3-Butadiene Hydrogenation over Au/ZrO2," Angewandte Chemie 45(41), pp. 6865-6868 (2006).
Loc, et al., "Kinetics of Propane and n-Butane Dehydrogenation over Platinumframe0Alumina Catalysts in the Presence of Hydrogen and Water Vapor," Kinetika i Kataliz (Kinetics and Catalysis) 37(60), pp. 790-796 (1996).
Loffreda, et al., "Tuning catalytic reactivity on metal surfaces: Insights from DFT," Journal of Catalysis 308, pp. 374-385 (2013).
Lozano, et al., "Influence of toluene on the catalytic activity of NiPdCe catalyst for selective hydrogenation of 1,3-butadiene," Fuel 110, pp. 76-82 (2013).
Lucci, F.R., et al., "Selective hydrogenation of 1,3-butadiene on platinum-copper alloys at the single-atom limit," Nature Communications, 6, 8550 (2015).
Massard, et al., "Strained Pd overlayers on Ni nanoparticles supported on alumina and catalytic activity for buta-1,3-diene selective hydrogenation," Journal of Catalysis 245(1), pp. 133-143 (2007).
Megumu, et al., "Dehydrogenation and Isomerization of Butane over Cr Catalysts Supported on H-SSZ-35 Type Zeolites," Bulletin of the Chemical Society of Japan 77(2), pp. 381-386 (2004).
Nagaraja, et al., "Selective and stable bimetallic PtSn/θ-Al2O3 catalyst for dehydrogenation of n-butane to n-butenes," Applied Catalysis A: General 467, pp. 211-223 (2013).
Nowinska, et al., "Propane oxydehydrogenation over transition metal modified zeolite ZSM-5," Applied Catalysis A: General 243(2), pp. 225-236 (2003).
Palacio, et al., "Catalytic performance and stability of isomorphic molybdates used for the oxidative dehydrogenation of propane," Reaction Kinetics and Catalysis Letters 85(1), pp. 175-182 (2005).
Palacio, et al., "Cu, Mn and Co molybdates derived from novel precursors catalyze the oxidative dehydrogenation of propane," Catalysis Today 107-108, pp. 338-345 (2005).
Pattamakomsan, et al., "Effect of mixed Al2O3 structure between 0- and a-Al2Oa on the properties of Pd/Al2O3 in the selective hydrogenation of 1,3-butadiene," Catalysis Communications 11(5), pp. 311-316 (2010).
Pattamakomsan, et al., "Selective hydrogenation of 1,3-butadiene over Pd and Pd—Sn catalysts supported on different phases of alumina," Catalysis Today 164(1), pp. 28-33 (2011).
Piccolo, et al., "Pd—Au single-crystal surfaces: Segregation properties and catalytic activity in the selective hydrogenation of 1,3-butadiene," Surface Science 592(1-3), pp. 169-181 (2005).
Piccolo, et al., "Tuning the shape of nanoparticles to control their catalytic properties: selective hydrogenation of 1,3-butadiene on Pd/Al2O3," Physical Chemistry Chemical Physics 10(36), pp. 5504-5506 (2008).
Qingjie, et al., "Oxidative dehydrogenation of ethane and propane over Mn-based catalysts," Catalysis Letters 68(1-2), pp. 59-62 (200).
Sadykov, et al., "Oxidative dehydrogenation of propane over monoliths at short contact times," Catalysis Today 61(1-4), pp. 93-99 (2000).
Seo, et al., "Direct dehydrogenation of n-butane over Pt/Sn/M/?-Al2O3 catalysts: Effect of third metal (M) addition," Catalysis Communications 47, pp. 22-27 (2014).
Seo, et al., "Direct Dehydrogenation of n-Butane Over Pt/Sn/Zn/?-Al2O3 Nano-Catalyst: Effect of Zn Content," Journal of Nanoscience and Nanotechnology 15(10), pp. 8318-8323 (2015).
Shashikala, et al., "n-Butane Dehydrogenation on PtSn/Carbon Modified MgO Catalysts," Catalysis Letters 143(7), pp. 651-656 (2013).
Silvestre-Albero, et al., "Atmospheric pressure studies of selective 1,3-butadiene hydrogenation on well-defined Pd/Al2O3/NiAl (110) model catalysts: Effect of Pd particle size," Journal of Catalysis 240(1), pp. 58-65 (2006).
Stern, et al., "Propane Oxyhydrogenation over Molybdate-based Catalysts," Journal of Catalysis 167(2), pp. 550-559 (1997).
Verdier, et al., "Pd—Sn/Al2O3 catalysts from colloidal oxide synthesis: 11. Surface characterization and catalytic properties for buta-1,3-diene selective hydrogenation," Journal of Catalysis 218(2), pp. 288-295 (2003).
Volpe, et al., "Butane dehydrogenation on vanadium supported catalysts under oxygen free atmosphere," Applied Catalysis A: General 272(1-2), pp. 69-78 (2004).
Wakui, et al., "Dehydrogenative Cracking of n-Butane over Modified HZSM-5 Catalysts," Catalysis Letters 81(1-2), pp. 83-88 (2002).
Watanabe, "Development of the new catalyst for propane selective dehydrogenation utilizing oxidation-reduction of the perovskite oxide catalyst," Petrotech, pp. 520-523 (2013).
Wu & Stair, "UV Raman spectroscopic studies of V/?-Al2O3 catalysts in butane dehydrogenation," Journal of Catalysis 237(2), pp. 220-229 (2006).
Wu, et al., "n-Butane dehydrogenation over Pt/Mg(In)(Al)O," Appliede Catalysis A: General 470, pp. 208-214 (2014).
Yan, et al., "Single-Atom Pd1/Graphene Catalyst Achieved by Atomic Layer Deposition: Remarkable Performance in Selective Hydrogenation of 1,3-Butadiene," Journal of the American Chemical Society 137(33), pp. 10484-10487 (2015).
Yi, et al., "Precisely Controlled Porous Alumina Overcoating on Pd Catalyst by Atomic Layer Deposition: Enhanced Selectivity and Durability in Hydrogenation of 1,3-Butadiene," ACS Catalysis 5(5), pp. 2735-2739 (2015).
Zhang, et al., "Catalysis by Gold: Isolated Surface Au3 Ions are Active Sites for Selective Hydrogenation of 1,3-Butadiene over Au/ZrO Catalysts," Angewandte Chemie 44(43), pp. 7132-7135 (2005).
Zhang, et al., "Comparative study of Au/ZrO2 catalysts in CO oxidation and 1,3-butadiene hydrogenation," Catalysis Today 122(3-4), pp. 330-337 (2007).
Zhang, et al., "Pd Cluster Nanowires as Highly Efficient Catalysts for Selective Hydrogenation Reactions," Chemistry: A European Journal 18(9), pp. 2639-2645 (2012).
Zhu, et al., "Study of Mn-based Catalysts for Oxidative Dehydrogenation of Cyclohexane to Cyclohexene," Catalysis Letters 105(1-2), pp. 29-33 (2005).

FIG. 1

FIG. 2A — Bare TiO₂

FIG. 2B — Fresh Zn/TiO₂

FIG. 2C — Spent low Zn/TiO₂

FIG. 2D — Fresh Mn/Zn/TiO₂

FIG. 2E — Spent Mn/Zn/TiO₂

SUPPORTED MULTIMETALLIC CATALYSTS FOR OXIDATIVE DEHYDROGENATION OF ALKANES

CROSS-REFERENCE TO RELATED APPLICATIONS

This application is a divisional of U.S. patent application Ser. No. 15/688,699, now U.S. Pat. No. 10,828,621, filed on Aug. 28, 2017, the content of which is herein incorporated by reference.

STATEMENT OF GOVERNMENT INTEREST

This invention was made with government support under Contract No. DE-AC02-06CH11357 awarded by the United States Department of Energy to UChicago Argonne, LLC, as operator of Argonne National Laboratory. The government has certain rights in the invention.

FIELD OF INVENTION

The present application relates generally to the field of multimetallic catalysts. In particular, the invention relates to a multimetallic catalyst for oxidative dehydrogenation of alkanes to olefins (alkenes) or diolefins (dienes), a method of synthesizing a multimetallic catalyst for oxidative dehydrogenation of alkanes to olefins (alkenes) or diolefins (dienes), and a method of performing oxidative dehydrogenation of alkanes to olefins (alkenes) or diolefins (dienes) in the presence of a multimetallic catalyst.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Practical and efficient catalyst technologies for alkane oxidative dehydrogenation (ODH) to value-added olefin products is a rapidly developing area in alkane conversion since the product is an important intermediate for polymers and commodity chemicals production.

Supported transition metal catalysts for oxidative dehydrogenation of alkanes to olefins (alkenes) or diolefins (dienes) deactivate due to facile agglomeration of the active sites during catalysis. Active site agglomeration not only leads to deactivation, but also results in pronounced changes in catalytic selectivity. For example, highly dispersed or isolated manganese oxide sites are more selective for alkane oxidative dehydrogenation, while the corresponding manganese oxide crystallites are good combustion catalysts, producing $CO_2$ as the main oxidation product. It is then crucial to stabilize site-isolated and/or highly dispersed manganese oxide oligomers on catalyst support surfaces under reaction conditions to suppress hydrocarbon deep oxidation (combustion) and maintain catalyst activity to the higher value olefin products, thereby increasing the efficiency of ODH catalysts.

Relative to direct, non-oxidative dehydrogenation of alkanes, catalytic ODH routes are thermodynamically more favored for the conversion of alkanes to the corresponding alkenes. Site-isolated mid-transition metal oxides (e.g., Mn, Cr) have been shown active and selective for this transformation; however, most of the known ODH catalysts suffer from aggressive deactivation due to active site sintering to form bulk phases (e.g., $Mn_2O_3$) that are more selective to combustion products (e.g., carbon oxides). A need exists for strategies for active site stabilization under ODH.

There remains no consensus strategy for stabilizing Mn- and Cr-based ODH sites as these metals are largely used as promoters for other redox-active cations (e.g., molybdenum). In most studies and reports on bulk manganese-oxide-based catalysts report ODH activities, however, stability issues remain unresolved. Site-isolation is key in tuning the selectivity of ODH catalytic sites. Most catalyst synthesis strategies reported in the prior art involving mid-transition metal ODH catalysts give a distribution of sites with varying reactivities, hence, impacting the overall reaction selectivity and efficiency.

SUMMARY

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

In some embodiments, a catalyst for oxidative dehydrogenation of alkanes includes a substrate including an oxide; at least one promoter including a transition metal or a main group element of the periodic table; and an oxidation-active transition metal. The catalyst is multimetallic.

In some aspects of the catalyst, the oxidation-active transition metal comprises manganese, nickel or vanadium.

In some aspects of the catalyst, the substrate is selected from the group consisting of $SiO_2$, $Al_2O_3$, $TiO_2$, and $ZrO_2$.

In some aspects of the catalyst, the at least one promoter comprises a Lewis acidic and redox-active promoter.

In some aspects of the catalyst, the at least one promoter comprises an oxide layer of the transition metal or the main group element of the periodic table having a general formula of $MO_x$, where M is the transition metal or the main group metal of the periodic table.

In some aspects of the catalyst, the at least one promoter is selected from the group consisting of Zn, Fe, Ga, Cr, Zr, Ni, and V.

In some aspects of the catalyst, the catalyst is doped with an element selected from the Group I elements of the periodic table, the Group II elements of the periodic table, or the main group elements of the periodic table.

In some embodiments, a method of producing an alkene includes providing an alkane; and performing oxidative dehydrogenation on the alkane in the presence of an oxidant (e.g., air or $CO_2$) and a catalyst to yield an alkene. The catalyst includes a substrate including an oxide; at least one promoter including a transition metal or a main group element of the periodic table; and an oxidation-active transition metal. The catalyst is multimetallic. The alkane and the oxidant are may be present in a 1:1 ratio.

In some embodiments, a method of synthesizing a catalyst for oxidative dehydrogenation of alkanes includes providing a substrate includes an oxide; reacting the substrate with at least one promoter to form an intermediary; and reacting the intermediary with an oxidation-active transition metal to form the catalyst. The at least one promoter includes a transition metal or a main group element of the periodic table. The catalyst is multimetallic.

In some aspects of the method, the oxidation-active transition metal comprises manganese, nickel or vanadium.

In some aspects of the method, the substrate is selected from the group consisting of $SiO_2$, $Al_2O_3$, $TiO_2$, and $ZrO_2$.

In some aspects of the method, the at least one promoter comprises a Lewis acidic and redox-active promoter.

In some aspects of the method, the at least one promoter comprises an oxide layer of the transition metal or the main group element of the periodic table having a general formula of $MO_x$, where M is the transition metal or the main group metal of the periodic table.

In some aspects of the method, the at least one promoter is selected from the group consisting of Zn, Fe, Ga, Cr, Zr, Ni, and V.

Some aspects of the method further include doping the catalyst with an element selected from the Group I elements of the periodic table, the Group II elements of the periodic table, or the main group elements of the periodic table.

In some aspects of the method, the oxidation-active transition metal is impregnated in a surface of the at least one promoter.

In some aspects of the method, the oxidation-active transitional metal is formed on a surface of the at least one promoter.

In some aspects of the method, the step of reacting the substrate with the at least one promoter and the step of reacting the intermediary with the oxidation-active transition metal are performed simultaneously.

In some aspects of the method, the step of reacting the substrate with the at least one promoter and the step of reacting the intermediary with the oxidation-active transition metal are performed sequentially.

In some aspects of the method, reacting the substrate with the at least one promoter comprises depositing the at least one promoter on a surface of the substrate via atomic layer deposition; and reacting the intermediary with the oxidation-active transition metal comprises depositing the oxidation-active transition metal on a surface of the intermediary via atomic layer deposition.

In some aspects of the method, reacting the substrate with the at least one promoter comprises performing solution-phase organometallic grafting or electrostatic adsorption; and reacting the intermediary with the oxidation-active transition metal comprises performing solution-phase organometallic grafting or electrostatic adsorption.

BRIEF DESCRIPTION OF THE DRAWINGS

The disclosure will become more fully understood from the following detailed description, taken in conjunction with the accompanying figures, in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

The present disclosure describes a method of synthesizing a multimetallic catalyst for oxidative dehydrogenation of alkanes to olefins. The alkanes may be, for example, gaseous alkanes. A general synthetic approach to oxidative dehydrogenation of alkanes using the catalysts of the present disclosure is shown below.

Reaction Scheme I

In Reaction Scheme I above, catalyst $M'/M/E_xO_y$ comprises an oxidation-active transition metal, (M'), at least one promoter (M) comprising a transition metal or main group element, and a substrate surface ($E_xO_y$). The oxidation-active transition metal (M') is typically in an oxidized form. In the presence of $O_2$ (air) and the catalyst $M'/M/E_xO_y$, the alkane undergoes oxidative dehydrogenation to produce an olefin (alkene). In the example above, although air is described as the oxidant for the oxidative dehydrogenation process, the concepts disclosed herein are not limited in this regard. In other examples, other oxidants (e.g., $CO_2$ may be used). In the example above, although the alkane is propane and the olefin is propylene (propene), the concepts disclosed herein are not limited in this regard. In other examples, different alkanes (e.g., C2 to C12) may be used to produce different olefins or diolefins. For example, n-butane may undergo oxidative dehydrogenation in the presence of $O_2$ (air) and the catalyst $M'/M/ExOy$ to produce 1,3-butadiene. Modified oxide supports equipped with transition metal or main group element promoters are employed for tuning the activity, selectivity and stability of the ODH active site.

In one example, a synthetic approach in forming the catalyst of the present disclosure is shown below.

Reaction Scheme II

In the Reaction Scheme II above, L and L' may be a surface oxygen anion or an organic ligand/capping group.

The substrate surface comprises a support material with the general formula of $E_xO_y$. In some implementations, the support material is selected from an oxide substrate such as zirconia ($ZrO_2$), titania ($TiO_2$), silica ($SiO_2$) or alumina ($Al_2O_3$), or the like. Further, the substrate may comprise a substrate surface composed of any of the preceding. The substrate surface may be a high-surface-area substrate. The substrate surface may be formed as a membrane, as a particle (e.g. a bead or powder), or as some other structure. The substrate surface may be a porous body. In various embodiments the substrate surface has a surface area, incrementally, of at least 1 $m^2/g$, at least 5 $m^2/g$, at least 10 $m^2/g$, at least 20 $m^2/g$, at least 40 $m^2/g$, at least 60 $m^2/g$, at least 80 $m^2/g$, and/or at least 100 $m^2/g$. In some embodiments, the substrate surface has a surface area, incrementally, of up to about 10000 $m^2/g$, up to 5000 $m^2/g$, up to 1000 $m^2/g$, up to 500 $m^2/g$, up to 250 $m^2/g$, up to 150 $m^2/g$, up to 120 $m^2/g$, up to 100 $m^2/g$, up to 80 $m^2/g$, and/or up to 60 $m^2/g$. In other embodiments, substrate surface may have a surface area of more than 10,000 $m^2/g$ or less than 1 $m^2/g$. The supports may be microporous, mesoporous, non-porous or macroporous in various implementations. Particles of the substrate surface may be of any size appropriate for the scale of the structure.

The promoter comprises a transition metal or main group element (M). Promoters significantly suppress coke deposition under harsh reaction conditions (e.g., 200° C. or higher). Moreover, metal oxide promoters improve catalyst stability and in some implementations, are recyclable after multiple-cycle oxidative dehydrogenations. The transition metal may be, in some implementations, a first row transition metal such as zinc or iron. The main group element may be, in some implementations, gallium. In some implementations, the promoter comprises an oxide layer of the transition metal or main group element having the general formula $MO_x$, where M is a transition metal or main group metal. Specifically, $MO_x$ may include, but is not limited to, $TiO_2$, $ZrO_2$, $CoO_x$ (where x ranges between 1 and 1.5), ZnO, $MnO_x$ (where x ranges from 1 to 3), $B_2O_3$, $Al_2O_3$, and $Ga_2O_3$. The promoter may be a Lewis acidic and redox-active promoter. In some examples, the catalyst may be a trimetallic catalyst including a plurality of promoters. For example, a trimetallic catalyst may include manganese promoted by nickel and zinc.

The promoter has a thickness. For example, the promoters may be installed as a submonolayer, a full monolayer, or as multilayers (e.g., 2 to 20 layers). In one implementation, the promoter does not provide complete coverage of the substrate surface. For example, the promoter may be deposited by a thin film deposition technique to form a partial monolayer atop the substrate surface. In another implementation, a complete monolayer of the promoter is formed. In yet another implementation, the promoter may include at least 2 layers, at least 3 layers, at least 4 layers, at least 5 layers, and/or at least 10 layers. In some implementation, the promoter comprises multiple metals or metal oxides. In other implementations, the promoter consists essentially of a single transition metal, a single main group element, or a single metal oxide.

The catalytic metal (M') includes a catalytically active material. In particular, M' is an oxidation-active transition metal including, but not limited to, manganese, nickel, or vanadium. The catalytic metal (M') is typically installed in an oxidized form, as opposed to an elemental form. In some implementations, the catalytic metal consists essentially of one of manganese, nickel or vanadium. In other implementations, the catalytic metal consists of one of manganese-containing material, nickel-containing material, or vanadium-containing material. The catalytic metal (M') may be present on a surface of the promoter (M) or impregnated within the promoter (M).

In some implementations, the promoter (M) and the catalytic metal (M') may be the same transition metal (e.g., in implementations using dimeric sites). In other implementations, the promoter (M) and the catalytic metal (M') are different transition metals.

Various synthesis methods may be used for depositing the promoter (M) and the catalytic metal (M'). For example, synthesis methods may include thin-film deposition techniques, such as Atomic Layer Deposition (ALD), solution processes (Sol'n) or strong electrostatic adsorption (SEA). In other words, in the catalyst formation steps of Reaction Scheme II, the promoter (M) and the catalytic metal (M') may be installed or deposited on the substrate surface via (a) gas-phase deposition (e.g., atomic layer deposition (ALD)) at a temperature, for example, from 50 to 400° C., (b) solution-phase organometallic grafting at room temperature, (c) strong electrostatic adsorption, or (d) a combination thereof. In some implementations, one or more of the catalytic metal (M'), the promoter (M) and the substrate surface can be formed by ALD. ALD utilizes alternating exposures between precursors (i.e. in a gaseous form) and a solid surface to deposit materials in a monolayer-by-monolayer fashion. This process can provide uniformity of the coatings in many embodiments, including on nanoporous substrate materials. A catalyst system may be manufactured using a combination of deposition methods. Further, the number of cycles for each deposition, for example, the number of ALD cycles, may be varied. In some implementations, this process also allows good control over the thickness and composition of the coatings. In one embodiment, ALD may be used to deposit both the promoter (M) and the catalytic metal (M'). In another implementation, ALD may be used to deposit the promoter (M) and a solution-phase process may be used to deposit the catalytic metal (M'). In yet another implementation, SEA may be used to deposit the promoter (M) and a solution-phase process may be used to deposit the catalytic metal (M').

Although Reaction Scheme II illustrates the promoter (M) being installed on the substrate surface prior to the catalytic metal (M') being installed, in other implementations, Reaction Scheme II may be modified such that the catalytic metal (M') is installed prior to depositing the promoter (M) or such that the catalytic metal (M') and the promoter (M) are installed simultaneously. When gas-phase synthesis is used in the catalyst formation, deposition is performed in two steps: one step to deposit the promoter (M) and another step to deposit the catalytic metal (M'). A purge step in the presence of an inert gas may be performed between the two steps. Moreover, one deposition step may be performed at the same or different temperature conditions than the other deposition step. When solution-phase synthesis is used in the catalyst formation, the promoter (M) and the catalytic metal (M') may be installed sequentially or simultaneously.

In some implementations, the catalysts disclosed herein may be formed as a promoter deposited on the substrate and a catalytic metal deposited on the promoter. In other implementations, the promoter and the catalytic metal may be interchanged by being introduced to the substrate surface simultaneously. In some implementations, the catalytic metal and the promoter may be discrete layers. In further implementations, the catalytic metal and/or the promoter are each a monolayer or sub-monolayer. In some implementations, the catalytic metal and/or the promoter each may include multiple layers. In some implementations, the catalytic metal and/or the promoter each may include at least 2 layers, at least 3 layers, at least 4 layers, at least 5 layers, and/or at least 10 layers. In other implementations, the catalytic metal and/or the promoter are each formed of isolated sites or extended structures such as clusters, islands, particles, or flakes. In a preferred implementation, the catalytic metal and/or the promoter are each formed of isolated sites or small clusters. The catalyst may, in some implementations, be doped/incorporated with Group I or Group II, or main group elements. For example, the catalyst may be doped with alkali elements (e.g., Li, Na, or K), alkaline earth elements (e.g., Mg or Ca), metalloids (e.g., B), or post-transition metals (e.g., Sn).

In conventional oxidative dehydrogenation reaction schemes (i.e., without the catalysts of the present application) to convert an alkane to an olefin, a ratio of the concentration of the alkane to the concentration of $O_2$ is approximately 2:1 and the reaction is carried out at a temperature less than 400° C. In such conventional oxidative dehydrogenation reaction schemes, about 8% of the propane is converted. The propylene yield is approximately 3.5%. The selectivity to propylene is about 40% at 8% conversion.

In contrast, performing oxidative dehydrogenation using the catalysts of the present application, a ratio of the concentration of the alkane to the concentration of 02 is approximately 1:1. This ratio allows for a more compact reactor design. Moreover, using the catalysts of the present application, the reaction can be carried out at a higher temperature than the conventional oxidative dehydrogenation reaction schemes, for example, at a temperature up to 500° C. Some of the catalysts tested (described in further detail below), exhibit overall ODH selectivities to propylene as high as 90% at 10 to 15% conversion, and propylene yields of 7 to 15% at 500° C. Table 1 below summarizes the propylene yield at 500° C. for the catalyst formulations of Examples 1-8.

TABLE 1

| Example | Catalyst Formulation | Propylene Yield (%) at 500° C. |
|---|---|---|
| 1 | Mn/Cr/SiO$_2$ | 7.3 |
| 2 | Mn/Zr/SiO$_2$ | 7.7 |
| 3 | Mn/Ni/Al$_2$O$_3$ | 8.0 |
| 4 | Mn/Ni/TiO$_2$ | 9.8 |
| 5 | Mn/Ni/SiO$_2$ | 10.8 |
| 6 | Mn/N/ZrO$_2$ | 12.0 |
| 7 | Mn/Ni/ZrO$_2$ | 13.0 |
| 8 | Mn/V/Al$_2$O$_3$ | 13.1 |

In Example 1 of Table 1, the Cr may have a specific surface coverage of approximately 10% of a monolayer. In Example 2 of Table 1, the Zr may have a specific surface coverage of approximately 10% of a monolayer. In each of Examples 3 and 4 of Table 1, the Ni may have a specific surface coverage of approximately 23% of a monolayer. In Example 5 of Table 1, the Ni may have a specific surface coverage of approximately 20% of a monolayer. In Example 6 of Table 1, the Ni may have a specific surface coverage of approximately 100% of a monolayer. In Example 7 of Table 1, the Ni may have a specific surface coverage of approximately 50% of a monolayer. In Example 8 of Table 1, the V may have a specific surface coverage of approximately 50% of a monolayer.

Figure 1:
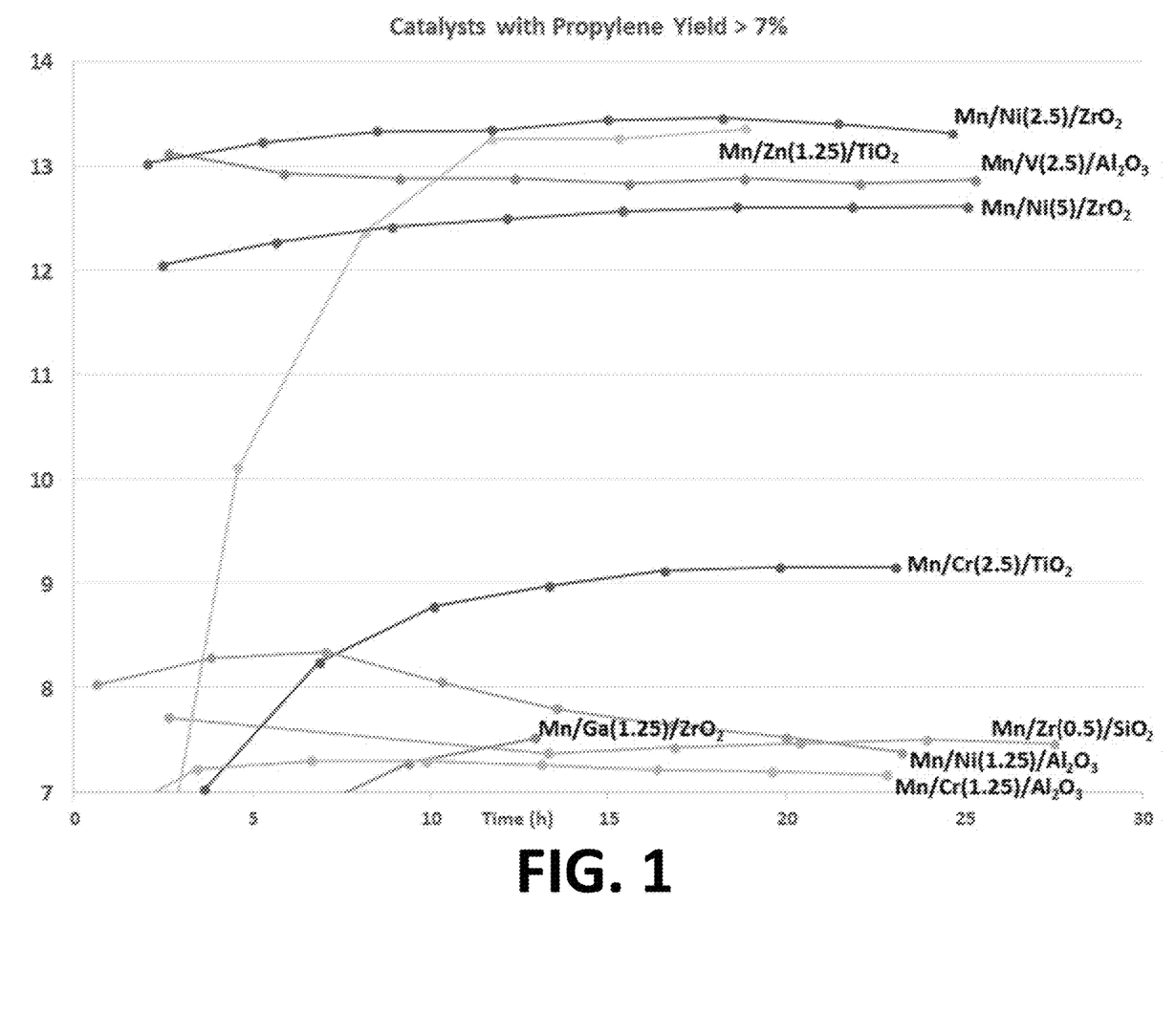
FIG. 1 is a graph illustration the propylene yield of various examples of multimetallic catalysts synthesized in accordance with the embodiments of the invention.
Figure 2A:
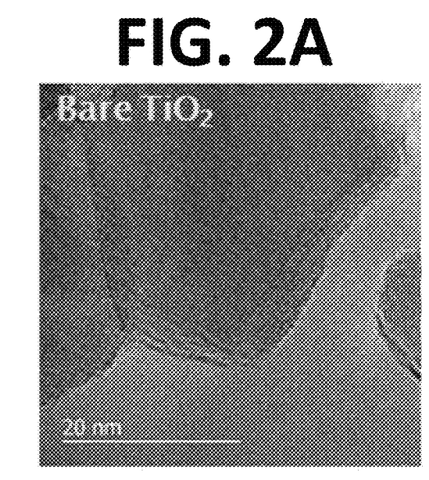
FIG. 2A is a microscopic image of a bare $TiO_2$ catalyst.
Figure 2B:
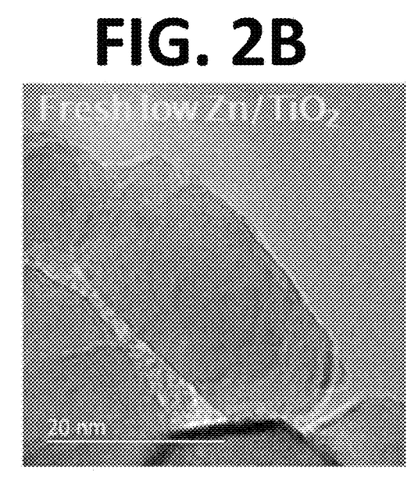
FIG. 2B is a microscopic image of a fresh low $Zn/TiO_2$ catalyst.
Figure 2C:
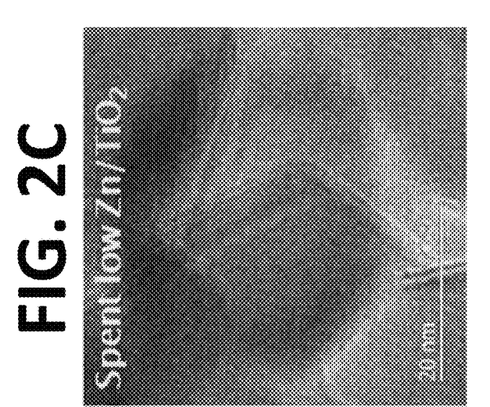
FIG. 2C is a microscopic image of a spent low $Zn/TiO_2$ catalyst.
Figure 2D:
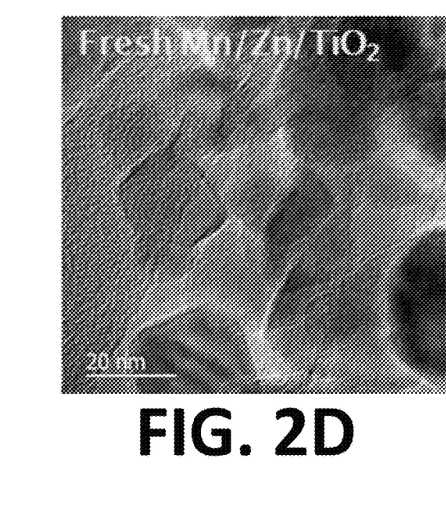
FIG. 2D is a microscopic image of a fresh $Mn/Zn/TiO_2$ catalyst.
Figure 2E:
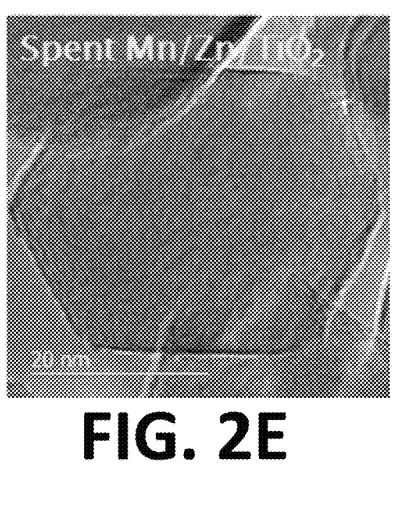
FIG. 2E is a microscopic image of a spent $Mn/Zn/TiO_2$ catalyst.
Figure 3A:
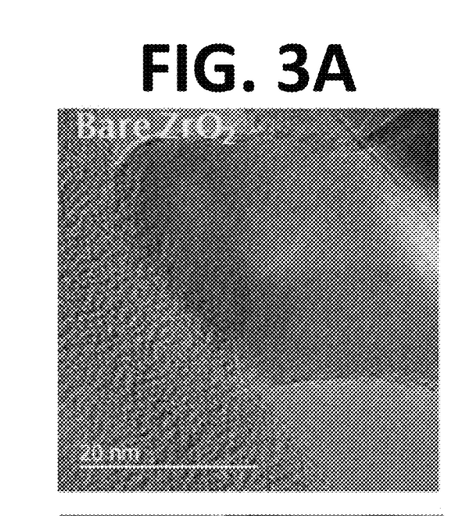
FIG. 3A is a microscopic image of a bare $ZnO_2$ catalyst.
Figure 3B:
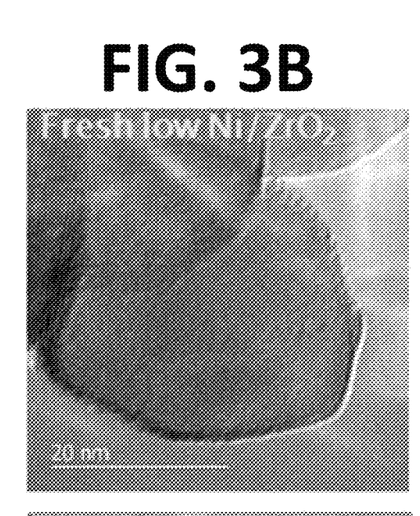
FIG. 3B is a microscopic image of a fresh $Ni/ZrO_2$ catalyst.
Figure 3C:
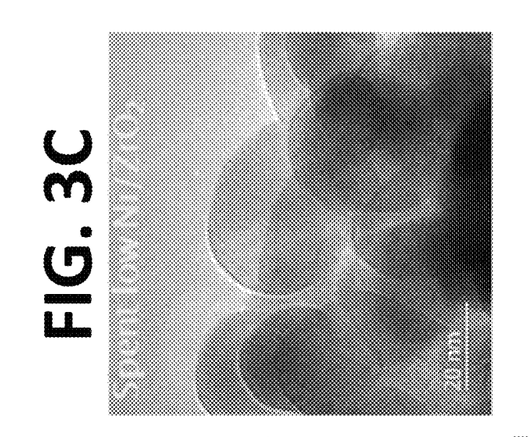
FIG. 3C is a microscopic image of a spent $Ni/ZrO_2$ catalyst.
Figure 3D:
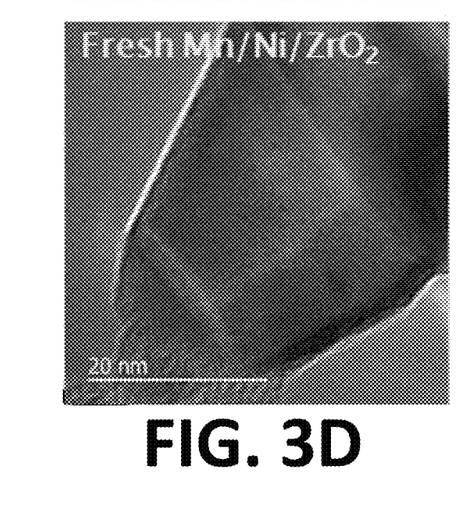
FIG. 3D is a microscopic image of a fresh $Mn/Ni/ZrO_2$ catalyst.
Figure 3E:
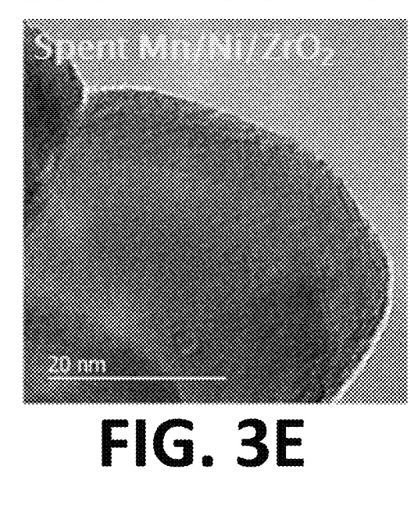
FIG. 3E is a microscopic image of a spent $Mn/Ni/ZrO_2$ catalyst.

As discussed above, most ODH catalysts aggressively deactivate due to site agglomeration and excessive coke deposition. In order to verify the stability of the catalysts, the propylene yield was observed at 500° C. for at least 25 hours. FIG. 1 is a graph illustrating the propylene yield of various catalyst formulations (formed in accordance with the implementations of this application) over time. As seen in FIG. 1, the catalysts exhibit long term stability in that the propylene yield does not approach zero over time.

Moreover, as seen in a comparison of FIGS. 2A-2E and FIGS. 3A-3E, the catalysts according to the implementations of the invention (see FIGS. 2D, 2E, 3D and 3E) did not exhibit evidence of nanoparticles forming. In other words, there was no evidence of site agglomeration or excessive coke deposition in the spent catalysts.

The implementations above describe methods for synthesizing multimetallic catalysts, and methods for performing oxidation dehydrogenation of alkanes with multimetallic catalysts. In particular, the implementations described herein are directed to the synthesis of highly dispersed transition metal catalysts for alkane oxidative dehydrogenation on various solid oxide supports, and provide stability for the active sites of the catalysts under reaction conditions, thereby preventing the formation of bulk manganese oxide sites that compromise process selectivity to the desired product. The methods enforce site-isolation and employ cationic anchoring sites and promoters that enhance the long-term stability of Mn-based or Ni-based active sites. The multimetallic catalysts described herein are configured for the selective dehydrogenation of alkanes to olefins (e.g., propane ODH to propylene).

The construction and arrangements a multimetallic catalyst for oxidative dehydrogenation of alkanes to olefins or diolefins, a method of synthesizing a multimetallic catalyst for oxidative dehydrogenation of alkanes to olefins or diolefins, and a method of performing oxidative dehydrogenation of alkanes to olefins or diolefins in the presence of a multimetallic catalyst, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, image processing and segmentation algorithms, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

What is claimed:

1. A catalyst for oxidative dehydrogenation of alkanes, the catalyst comprising:
   a substrate comprising an oxide;
   at least one promoter selected from the group consisting of Cr, Zr, Ni, and V; and
   an oxidation-active transition metal,
   wherein the oxidation-active transition metal is dispersed on at least the promoter, the oxidation-active transition metal comprising Mn, and
   wherein the catalyst is multimetallic.

2. The catalyst of claim 1, wherein the substrate is selected from the group consisting of $SiO_2$, $Al_2O_3$, $TiO_2$, and $ZrO_2$.

3. The catalyst of claim 1, wherein the catalyst is doped with an element selected from the Group I elements of the periodic table, the Group II elements of the periodic table, or the main group elements of the periodic table.

4. A method of producing an alkene comprising:
   providing an alkane; and
   performing oxidative dehydrogenation on the alkane in the presence of an oxidant and the catalyst of claim 1 to yield an alkene.

5. The method of claim 4, wherein the alkane and the oxidant are present in a 1:1 ratio.

* * * * *